United States Patent
Steinberg-Shapira et al.

(10) Patent No.: US 9,826,929 B2
(45) Date of Patent: Nov. 28, 2017

(54) METHOD AND DEVICE FOR STUTTERING ALLEVIATION

(71) Applicant: NINISPEECH LTD., Haifa (IL)

(72) Inventors: Shirley Steinberg-Shapira, Haifa (IL); Yair Shapira, Haifa (IL)

(73) Assignee: NINISPEECH LTD., Haifa (IL)

( * ) Notice: Subject to any disclaimer, the term of this patent is extended or adjusted under 35 U.S.C. 154(b) by 285 days.

(21) Appl. No.: 14/372,458

(22) PCT Filed: Jan. 17, 2013

(86) PCT No.: PCT/IL2013/050048
§ 371 (c)(1),
(2) Date: Jul. 16, 2014

(87) PCT Pub. No.: WO2013/108255
PCT Pub. Date: Jul. 25, 2013

(65) Prior Publication Data
US 2015/0011842 A1    Jan. 8, 2015

Related U.S. Application Data

(60) Provisional application No. 61/587,869, filed on Jan. 18, 2012.

(51) Int. Cl.
*A61F 5/58* (2006.01)
*A61B 5/00* (2006.01)
(Continued)

(52) U.S. Cl.
CPC ........ *A61B 5/4803* (2013.01); *A61B 5/04886* (2013.01); *A61B 5/08* (2013.01);
(Continued)

(58) Field of Classification Search
CPC ..... A61F 5/58; A61B 5/4803; A61B 5/04886; A61B 5/4836; A61B 5/08; A61B 7/04;
(Continued)

(56) References Cited

U.S. PATENT DOCUMENTS

| 5,794,203 A | * | 8/1998 | Kehoe | ........... A61F 5/58 704/271 |
| 6,231,500 B1 | * | 5/2001 | Kehoe | ........... A61F 5/58 600/23 |

(Continued)

FOREIGN PATENT DOCUMENTS

WO    2011069095    6/2011

OTHER PUBLICATIONS

Czyzewski and Skorka (1996) Modification of the Auditory Loop-Effects on Hearing and Speech Production. 100th Audio Engineering Society Convention, Copenhagen, Denmark, May 1996, preprint No. 4148.
(Continued)

*Primary Examiner* — Charles A Marmor, II
*Assistant Examiner* — Thaddeus Cox
(74) *Attorney, Agent, or Firm* — The Roy Gross Law Firm, LLC; Roy Gross

(57) ABSTRACT

A device for stuttering alleviation is disclosed, comprising a speech sensor, configured to output signals indicative of speech, a processing unit configured to detect stuttering, log stuttering and/or produce stimulation indication based on stimulation rules Said device may further comprise a remote server and a server user interface, configured to allow the speech therapist access to the processing unit. Further provided is a method for accelerating the learning procedure for obtaining a permanent fluent speech, comprising receiving and analyzing speech parameters, determining whether a negative reinforcement is required and executing the negative reinforcement.

16 Claims, 3 Drawing Sheets

(51) Int. Cl.
*A61B 5/0488* (2006.01)
*A61B 5/08* (2006.01)
*A61B 7/04* (2006.01)

(52) U.S. Cl.
CPC .............. *A61B 5/4836* (2013.01); *A61B 7/04* (2013.01); *A61F 5/58* (2013.01)

(58) Field of Classification Search
CPC ........... A61B 5/12–5/128; A61B 5/40–5/4094; A61B 5/48–5/4896; A61B 5/72–5/7495; G09B 19/04
See application file for complete search history.

(56) References Cited

U.S. PATENT DOCUMENTS

| | | | |
|---|---|---|---|
| 6,423,013 B1* | 7/2002 | Bakker | A61B 7/00 600/529 |
| 6,754,632 B1 | 6/2004 | Kalinowski et al. | |
| 7,031,922 B1 | 4/2006 | Kalinowski | |
| 7,292,985 B2 | 11/2007 | Jiang | |
| 2003/0082507 A1* | 5/2003 | Stypulkowski | A61F 5/58 434/262 |
| 2006/0064037 A1 | 3/2006 | Shalon | |
| 2006/0183964 A1* | 8/2006 | Kehoe | A61F 5/58 600/23 |
| 2011/0257464 A1* | 10/2011 | Kehoe | A61F 5/58 600/23 |

OTHER PUBLICATIONS

Czyzewski et al., (2003) Intelligent processing of stuttered speech. Journal of Intelligent Information Systems 21(2): 143-171.
Howell and Williams (1992) Acoustic analysis and perception of vowels in children's and teenagers' stuttered speech. Journal of the Acoustical Society of America 91(3): 1697-1706.
Howell et al., (1998) Methods of interval selection, presence of noise and their effects on detectability of repetitions and prolongations. J Acoust Soc Amer 104(6): 3558-3567.
Howell P and Sackin S (1995) Automatic recognition of repetitions and prolongations in stuttered speech. In: Starkweather CW and Peters HFM (editors), Proceedings of the First World Congress on Fluency Disorders; Nijmegen, The Netherlands: University Press Nijmegen; pp. 372-374.
Kaczmarek and Skorka (1997) Investigation of the Pitch of the Vocal Tone for Stuttered Speech. 102nd Audio Engineering Society Convention, Munich, Germany, Mar. 1997, AES preprint No. 4486.
Ravikumar et al., (2009) An approach for objective assessment of stuttered speech using MFCC features. DSP Journal 9(1): 19-24.
Robb and Blomgren (1997) Analysis of F2 transitions in the speech of stutterers and non-stutterers. Journal of Fluency Disorders 22: 1-16.
Tan et al., (2007) Application of Malay speech technology in Malay Speech Therapy Assistance Tools. International on Conference Intelligent and Advanced Systems 2007, pp. 330-334.

* cited by examiner

METHOD AND DEVICE FOR STUTTERING ALLEVIATION

FIELD OF THE INVENTION

The present invention is generally directed toward a method for the treatment of stuttering. The method encompasses an automatic detection of stuttered speech and real-time stimulation for the person-who-stutters (PWS), as a mechanism to break the stuttering loop, create a time-out effect and accelerate the cognitive training to use new studied speech method.

BACKGROUND

Stuttering is a speech-fluency disorder, in which sounds, syllables or words are repeated or produced longer than normal. It can also include interjections of sounds or words, and unduly prolonged pauses. These disfluencies cause a significant break in the flow of speech. About 5% of children, aged 2-5, will develop some stuttering during their childhood years. In approximately 20% of these children exhibiting developmental stuttering, the speech disorder sustains and might worsen with age. The underlying etiology of stuttering is unknown, and it is considered to be a combination of genetic and environmental factors. In some cases, stuttering may develop in relation to central nerve system injuries (e.g., stroke or traumatic brain injuries), and in rare cases it may be associated with emotional trauma. The disorder may have significant developmental, communicational, social and vocational impacts on the person-who-stutters.

While there is disagreement about acceptable treatment outcomes from stuttering therapy, many treatments have been developed for stuttering and have been successful to varying degrees, such as speech-therapy techniques and electronic fluency devices. Most of the stuttering-therapy devices typically focus on altered auditory feedback. One of such marketed devices is the SpeechEasy, which is a wearable device that can be used in everyday life. The SpeechEasy alters sounds that go through the device so that the user can hear his or her voice at a slight time delay and/or at a different pitch. The purpose of the delay and pitch change is to recreate a natural phenomenon known as the "choral effect", which occurs while speaking or singing in unison with others, leading to a significant reduction or even elimination of stuttering. Other anti-stuttering devices provide visual alert for specific stuttering manifestations. However, the majority of these devices are not carried on human body. A tactile feedback prosthetic device, converting the stutterer's speech to vibrational signals is disclosed in U.S. application Ser. No. 289,766.

Conventional stuttering therapy anti-stuttering techniques are based on methods to regulate breathing and control the rate of speech, as stuttering is essentially a disorder manifested in poorly coordinated speech production muscles. Speech therapists equip their patients with various methods to attenuate their stutter. For example, one of the anti-stuttering techniques encompasses teaching the stutterers to speak in a mechanic shape, which usually enables a temporarily fluent speech. However, 84% of adults and teens reported experiencing a relapse after improving their fluency in therapy [NSA Survey Results 2009, web: 14 Sep. 2011, <http://www.westutter.org/stutteringInformation/NSA_Survey_Results.html>]. Six to twelve months (and sometimes more) are required for the people-who-stutter to practice this studied mechanic speech shape in order to achieve a permanently fluent and natural speech. The main challenge is in applying fluency methods continuously throughout the day and not only during clinical sessions or home training.

There is an unmet need for a device that can support the studied speech therapy techniques and accelerate the conversion of the achieved temporary fluency to a permanently fluent speech.

SUMMARY

The invention encompasses a method for accelerating the learning procedure for obtaining a permanent fluent speech. The invention further provides a device, configured to detect stuttering and/or to provide a stuttering log, for example, but not limited to, for analysis purpose. The device is further configured to provide stimulation upon the stuttering detection.

In one aspect, there is provided a device for alleviating stuttering, including a speech sensor configured to output a signal indicative of speech and a processing unit configured to receive the signal indicative of speech, detect stuttering and log stuttering and/or produce stimulation indication based on one or more stimulation rules.

According to some embodiments, the speech sensor includes a vocal cord compartment, an acoustical compartment, a breathing compartment or any combination thereof. The acoustic compartment may include a microphone. According to alternative embodiments, the acoustic compartment may include a throat microphone or a noise-cancelling microphone. According to further embodiments, the acoustic compartment may further include a mobile handset microphone. The vocal cord compartment may include a vocal cord activity sensor, including electromyograph (EMG), electroglottograph (EGG) or a combination thereof. The breathing compartment may include a breath volume sensor.

According to some embodiments, the processing unit is a standalone unit. According to the preferred embodiments, the processing unit is an application configured to run on a computer or a mobile device. According to the preferred embodiments, the processing unit is a standard mobile device application. Said mobile device may include operating system selected from the group consisting of iOS (Apple), Android (Google), Windows (Microsoft), QNX (RIM), Symbian (Accenture) and Linux. According to some embodiments, the mobile device is a mobile phone such as smartphone. Smartphones may include, for example, iPhones™ (available from Apple Inc., Cupertino, Calif.), BlackBerries™ (available from RIM, Waterloo, Ontario, Canada), or any mobile phones equipped with the Android™ platform (available, for example, from Google Inc., Mountain View, Calif. or Samsung Group, South Korea). According to other embodiments, the mobile device is a tablet computer, available from, for example, Apple, Samsung, HTC, Motorola, RIM, Sony, Amazon, HP, Microsoft, Google, Asus, Toshiba, and Archos. According to further embodiments, the mobile device may be a personal digital assistant (PDA).

According to further embodiments, the processing unit is configured to detect stuttering in real time. According to some embodiments, the stuttering detection may include determination of word spoken, phoneme spoken, stuttering mode, stuttering severity, stuttering level or any combination thereof. The stuttering mode may include prolongation, repetition, blocking, stress or any combination thereof. According to further embodiments, the processing unit is configured to allow determination of the detection parameters. According to yet further embodiments, the processing unit is configured to automatically identify detection parameters according to a stuttering log. According to still further embodiments, the stuttering detection parameters may include threshold length of prolongation, threshold number of repetitions, threshold length of blocking, threshold level of stress or any combination thereof. According to an important embodiment, the stuttering detection program is configured to allow the stuttering detection without elimination of background noise. According to some embodiments, the stuttering detection program is configured to detect stuttering no more than 500 ms following the stuttering event. According to the preferred embodiments, the stuttering detection program is configured to detect stuttering no more than 100 ms following the stuttering event.

According to some embodiments, stuttering logging may include saving and/or outputting stuttering occurrence parameters/characteristics. According to further embodiments, the stuttering occurrence parameters/characteristics may include a word spoken, a phoneme spoken, stuttering mode, stuttering severity, time of day, location or any combination thereof.

According to some embodiments, stuttering logging may include saving and/or outputting stuttering log. The stuttering log may include a word spoken, a phoneme spoken, stuttering mode, stuttering severity, stuttering confidence level, date, time of day, location or any combination thereof. According to further embodiments, stuttering logging may include saving and outputting speech related to stuttering. The speech related to stuttering may include the speech before, during and after the stuttering occurrence. According to some embodiments, the stuttering log may be used for analysis by a speech therapist and/or for research. According to further embodiments, the stuttering log is used for automatic determination of detection parameters. According to further embodiments, the stuttering log may be used to configure the stimulation rules.

According to some embodiments, the processing unit is configured to produce stimulation indication in real time. According to some embodiments, the stimulation indication includes stimulation activation indication, stimulation termination indication and stimulation parameters.

According to some embodiments the processing unit is further configured to transmit stimulation indication to a stimulator, configured to provide stimulation. According to some embodiments, the stimulator is a standalone unit. According to other embodiments, the stimulator and the speech sensor form one unit. According to some embodiments, the stimulator, the speech sensor or both may be worn on user's body. According to further embodiments, the stimulator is a mobile device. According to yet further embodiments, the mobile device is the device hosting the processing unit application.

According to some embodiments, the processing unit is configured to allow modulation of stimulation parameter. According to other embodiments, the stimulator is configured to allow modulation of stimulation parameters. The stimulation parameters may include type, intensity, mode, amplitude, frequency, duration, form, pattern or any combination thereof. The stimulator may include control panel for activation, termination and intensity modulation of the stimulation.

According to some embodiments, the stimulation type includes mechanic, electric, visual stimulation or any combination thereof. According to further embodiments, the mechanic stimulation may include steady, oscillatory, repeated, pulsatile or burst form. According to further embodiments, the electric stimulation may include DC current, AC current, steady, oscillatory, repeated, pulsatile or burst mode. According to some embodiments, the mechanic stimulation amplitude is from about 0.0001 to about 5 mm displacements. According to some embodiments, the mechanic stimulation frequency range is from about 1 to about 1000 Hz. According to other embodiments, the mechanic stimulation frequency is from about 50 to about 500 Hz. According to further embodiments, the electric stimulation frequency is from about 10 to 300 Hz. According to some embodiments, the electric stimulation form includes sinusoidal, square, triangular or sawtooth waveform. According to an important embodiment, the stimulation pattern is tailored to the user (person-specific).

According to further embodiments, the processing unit is configured to allow determination of stimulation rules, wherein the stimulation rules are based on one or more stuttering occurrence parameters/characteristics. According to further embodiments, the stuttering occurrence parameters/characteristics may include a word spoken, a phoneme spoken, stuttering mode, stuttering severity, time of day, location or any combination thereof. The stimulation rules may further be configured based on the probability of stimulation occurrence.

In some embodiments of the invention, the processing unit includes a user interface. The user interface may be configured to provide control of activation and/or termination of stuttering detection. The user interface may further be configured to provide control of activation and/or termination of stimulation. The user interface may further be configured to provide control of activation and/or termination of speech related to stuttering recording and/or stuttering logging.

According to some embodiments, the user interface is configured to provide indication of stuttering. According to still further embodiments, the user interface is configured to allow determination of parameters related to the stuttering log, stuttering detection, speech related to stuttering recording or any combination thereof. According to yet further embodiments, the user interface is configured to allow determination of parameters related to the stimulation parameters, stimulation rules or any combination thereof. The user interface may be further configured to allow deletion of preceding recording of the speech related to stuttering. According to some embodiments, the user interface is configured to present the stuttering log, speech related to stuttering recording or a combination thereof. The user interface may further be configured to provide metric for stuttering severity analysis. The user interface may further be configured to provide tools for assessing the severity of stuttering. According to further embodiments, the user interface may further be configured to provide metric for stuttering level analysis. According to further embodiments, the user interface may further be configured to determine stuttering level. According to further embodiments, the user interface is configured to present stuttering trends. According to some embodiments, the user interface is configured to provide visual stimulation.

In some embodiments of the invention, the speech sensor is configured to be worn on a user's body. In other embodiments of the invention, the stimulator is configured to be worn on a user's body. According to further embodiments, the speech sensor and the stimulator form one unit.

According to some embodiments, the device for stuttering alleviation further includes a remote server configured to receive recorded speech related to stuttering and the stuttering log from the processing unit. The remote server is further configured to store recorded speech related to stuttering and stuttering log received from the processing unit. According to further embodiments, the remote server is configured to transmit data related to stimulation rules, stimulation parameters and stuttering detection parameters to the processing unit. According to some embodiments, the remote server may be a servers farm or a computing cloud.

According to some embodiments, the remote server is configured to act as a license server. The remote server may be configured to provide licenses to the processing unit application. The remote server may further be configured to provide licenses to the server user interface application.

According to further embodiments, the device for stuttering alleviation further includes a server user interface configured to communicate with the remote server. According to some embodiments, the server user interface is a remote user interface. The server user interface may be configured to receive recorded speech related to stuttering and stuttering log from the remote server. The server user interface may further be configured to transmit data related to stimulation rules, stimulation parameters and stuttering detection parameters to the remote server. According to further embodiments, the server user interface is a web application configured to run on a servers farm or a computing cloud. According to some embodiments, the server user interface is a standard web application.

According to further embodiments, the server user interface is configured to allow determination of the stuttering log parameters, speech related to stuttering recording, stuttering detection parameters or any combination thereof. According to still further embodiments, the server user interface is configured to allow determination of the stimulation rules, stimulation parameters or any combination thereof.

According to some embodiments, the server user interface is configured to allow monitoring of the user's speech. According to further embodiments, the server user interface is configured to present stuttering log. According to some embodiments, the server user interface is configured to provide metric for stuttering severity analysis. The server user interface may further be configured to present stuttering trends. According to further embodiments, the server user interface may be configured to provide graphical representation of stuttering trends. According to important embodiments, the server user interface is configured to allow a speech therapist to use the stuttering log for analysis and research. According to some embodiments, the server user interface is configured to provide a database of stuttering log and speech related to stuttering recordings.

In another aspect, the invention provides a method for alleviating stuttering, including obtaining a signal indicative of the speech, detecting stuttering, and logging stuttering and/or producing stimulation based on one or more stimulation rules.

In yet another aspect, the invention provides a method for accelerating the learning procedure for obtaining a permanent fluent speech including receiving a set of parameters corresponding to the user's speech, analyzing the set of parameters and determining whether a negative reinforcement is required, and executing the negative reinforcement. According to further embodiments, the analyzing of the set of parameters is performed in a real time. According to some embodiments, the method is applied to alleviate stuttering. According to other embodiments, the method is applied to alleviate speech disorders other than stuttering. The speech disorders may include wrong generation of glottal wave due to over- or under-breathing, and wrong generation of specific syllables.

BRIEF DESCRIPTION OF THE FIGURES

Examples illustrative of embodiments of the invention are described below with reference to figures attached hereto. Dimensions of components and features shown in the figures are generally chosen for convenience and clarity of presentation and are not necessarily shown to scale. The figures are listed below.

DETAILED DESCRIPTION

The present invention is directed to the method for accelerating the learning procedure for obtaining a permanent fluent speech. The present invention is further directed to a device for stuttering alleviation (DSA).

Figure 1:
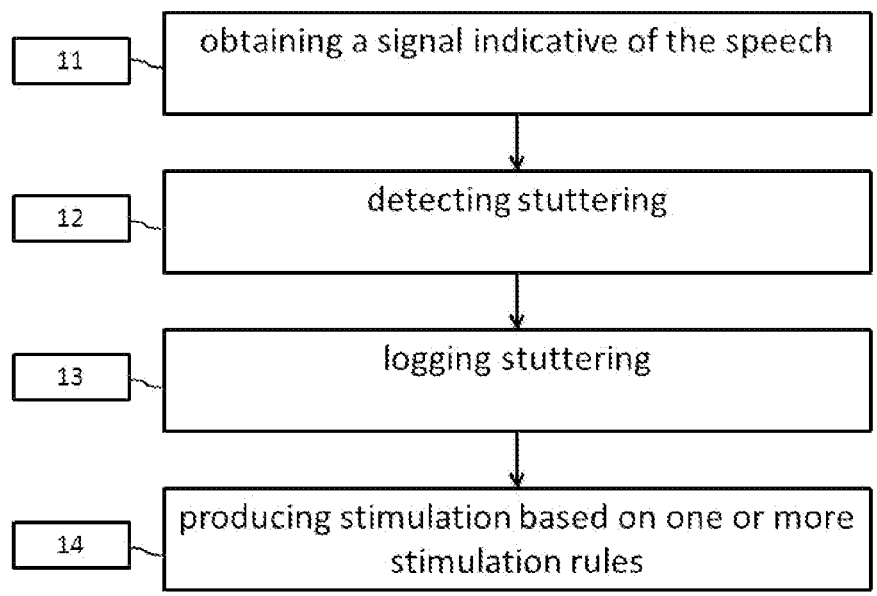
FIG. 1 schematically illustrates a flow chart of an exemplary method for stuttering alleviation.

Reference is made to FIG. 1 which schematically illustrates a flow chart of an exemplary method for stuttering alleviation, in accordance with an embodiment of the invention. The claimed method allows maintaining the studied speech fluency and accelerating the learning procedure for obtaining a permanent fluent speech.

[STEP 11] Speech production parameters are sensed by the device and a signal indicative of the speech is obtained.

[STEP 12] The signal indicative of speech is processed and analyzed in order to detect stuttering or stuttering attempt.

[STEP 13] Stuttering is logged. Stuttering logging comprises saving and/or outputting parameters related to stuttering and, optionally, speech related to stuttering. The parameters related to stuttering may include a word spoken, a phoneme spoken, stuttering mode, stuttering severity, stuttering confidence level, date, time of day and/or location. The stuttering logging may further include recording the speech related to stuttering, including the speech before, during and after the stuttering occurrence. The personal stuttering occurrence log may be used for analysis by the speech therapist and the anonymous log for research purposes. The stuttering log may further be used to manually or automatically configure the stimulation rules.

[STEP 14] Stimulation is produced according to stimulation rules. Stimulation rules may be configured based on stuttering occurrence parameters and/or stuttering occurrence characteristics. Stimulation of user is carried out by the device to stop the loop of stuttering. The negative reinforcement also accelerates the cognitive mechanisms to adopt the temporary fluency as a natural speech.

According to alternative embodiments of the invention, said method may be implemented to treat additional speech disorders, such as, but not limited to wrong generation of glottal wave due to over- or under-breathing, and wrong generation of specific syllables (e. g. "s" and "sh").

Figure 2:
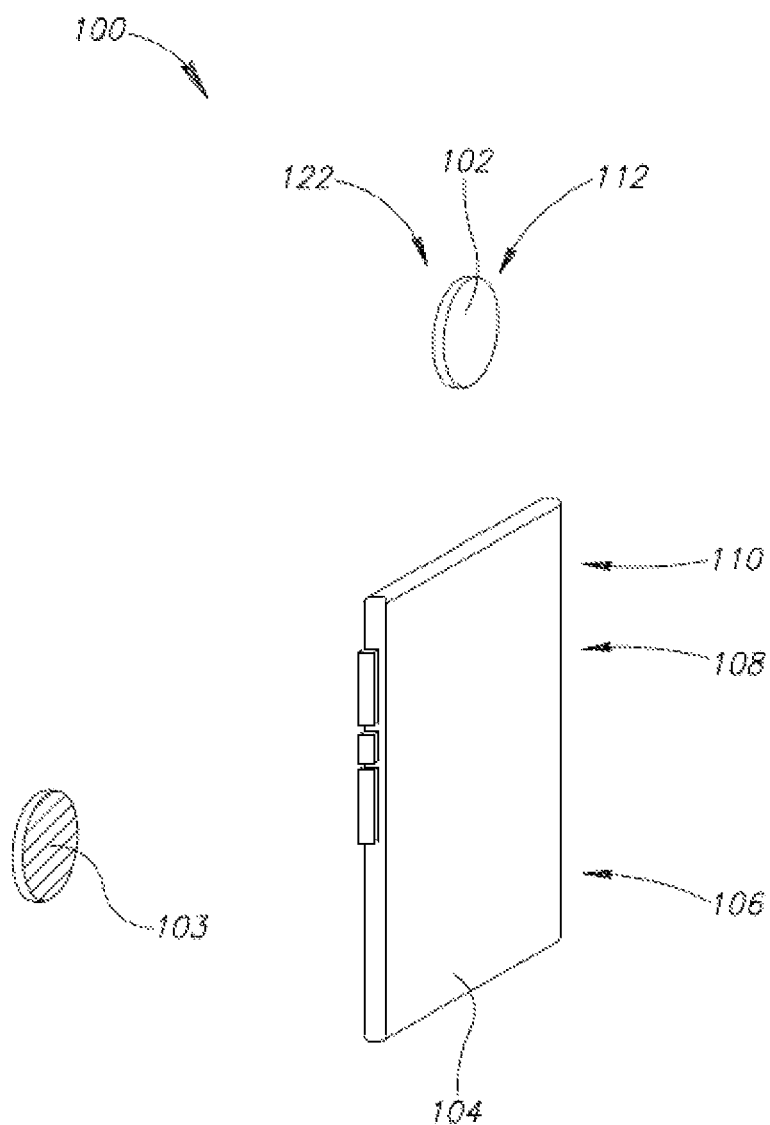
FIG. 2 schematically illustrates the components of the device for stuttering alleviation.

Reference is made to FIG. 2 which schematically illustrates the components of the device for stuttering alleviation (DSA), in accordance with an embodiment of the invention. The claimed device is configured to maintain the studied speech fluency and accelerate the learning procedure for obtaining a permanent fluent speech.

Device for stuttering alleviation 100 includes speech sensor 102, configured to output the signal indicative of speech; processing unit 104, configured to receive said signal, to identify stuttering or stuttering attempt and produce stimulation indication based on one or more predetermined rules; and stimulator 103, configured to provide stimulation according to an indication received from the processing unit.

According to one embodiment, speech sensor 102 comprises acoustic compartment 122 and optionally vocal cord compartment 112.

According to some embodiments, vocal cord compartment 112 includes a vocal cord activity detector, such as electromyograph (EMG), electroglottograph (EGG) or a combination thereof. EMG is a system that measures the electrical activities of muscles through electrodes attached to a person's body. EGG records the opening and closing of a person's vocal folds. EGG employs two electrodes on a person's neck and measures the resistance between the electrodes. This resistance changes as the vocal folds open and close. An EGG can show the frequency of the vocal folds, as well as the glottal wave form. This is the fundamental glottal wave of the speaker, without the harmonics produced by the nasal cavities, mouth, and the like.

According to further embodiments, acoustic compartment 122 includes a sound detector, such as microphone, noise-cancelling microphone or throat microphone. The acoustic compartment may further include a mobile handset microphone. The acoustic compartment is configured to receive acoustic signals and convert them to electronic signals indicative of speech. Other devices adapted to detect the pre-stuttering symptoms may be employed as sound detectors.

According to further embodiments, the speech sensor may include other detectors configured to identify other pre-stuttering symptom measures such as, but not limited to heart rate.

The input from acoustic compartment 122 and optionally vocal cord compartment 112 is transferred to processing unit 104. The processing unit is configured to process the speech-related signals and to identify in real time the stuttering events, modes and their severity. Stuttering types may be selected from, but not limited to prolongation, repetition, blocking and stress. The processing unit is configured to allow a real-time consideration if stimulation has to be carried out. It is further adapted to configure the stimulation type, such as, but not limited to stimulation location on the PWS's body, intensity, duration and frequency and to transmit the stimulation indication to mechanical and/or an electrical stimulator 103. According to some embodiments, processing unit 104 includes: a program for identifying the stuttering and its type, in real time based on the speech digital signals and a program for real time decision on generating stimulation and its type based on the stuttering type and level. The DSA is configured to be worn on the user's body or carried along by the user.

Stimulator 103 is configured to allow the stimulation to be applied to the stutterer's neck or any other organ that is found to be more effective and safe. According to the preferred embodiments, stimulator 103 is a tactile stimulator. The tactile stimulator is configured to provide mechanic and/or electric stimulation. The tactile stimulator may include mechanic or electric actuators, such as, but not limited to electrical tactors, piezoelectric actuators, rotary internal actuators, linear actuators and pneumatic tactors.

According to some embodiments of the invention, tactile stimulation generated by stimulator 103 may include a non-invasive stimulation applied at a predetermined range of intensities, frequencies, waveforms, patterns, durations, duty-cycles, locations and interstimulus intervals. Mechanic and/or electric stimulator may operate in a single mode or in multiple modes. It may be steady, oscillatory, repeated, pulsatile, burst or the like. The electric stimulator may further include a DC mode or an AC mode.

The stimulation is applied at predetermined intensities complying with stuttering modes detected by the processing unit. According to further embodiments, the stimulation is applied randomly or at a predetermined sequence of stuttering events, for example in one (1) out of ten (10) events or in 10 percent of events.

The mechanical stimulation frequency may include a spectral range from about 1 to about 1000 Hz, for example, about 1-100 Hz, about 50-300 Hz, about 300-500 Hz, about 500-800 Hz or about 800-1000 Hz. Mechanical stimulation amplitude range may be from about 0.0001 to 5 mm displacements. Mechanic stimulation pulse is preferably in the range of about 10 to 10000 µs in duration and is characterized by about 5% to about 50% duty cycle.

Mechanic actuators employ stimulation of mechanoreceptors in the user's skin. Mechanical stimulation may include various mechanisms, such as but not limited to pressure, temperature, skin stretch, or combinations thereof. In some variations the stimulation may include a mechanical force against the subject's skin at a predetermined frequency for a predetermined period of time. The temporal characteristics of the mechanical stimulation may be specific to the constant or varying targeted skin area. Varying the location of the stimulation every pre-defined time period (such as day or week) during the use of the device, may be beneficial to ensure that a neuroplasticity effect will not occur. According to some embodiments, the frequency of stimulation is varying or non-constant. According to other embodiments, the frequency is constant. In general the frequency refers to the frequency of the pulsatile stimulation during the time at which the stimulation is turned on. The force with which the mechanical stimulation is applied may also be constant or variable. Varying the force and/or frequency may be beneficial to ensure that the mechanical stimulation is effective during the entire period of stimulation, particularly if the effect of non-invasive stimulation operates at least in part through mechanoreceptors such as the rapidly acclimating Pacinian or Messiner corpuscles.

According to some embodiments of the invention the electric stimulator includes an electric source that transmits an electrical current to skin-attached electrodes. According to some embodiments of the invention, the distance between the electrodes is less than 2.5 cm. According to the preferred embodiments, the distance between the electrodes is less than 1 cm. The electric stimulator further may further include a stimulus isolation transformer, limiting the output pulse width to about 2 ms under 500 Ohm load conditions. According to some embodiments, the energy per pulse is limited to 300 mJ under 500 Ohm load conditions. The pulse maximum output voltage should not exceed a peak value of 500V under closed circuit conditions.

The electric current may be applied in various waveforms, such as but not limited to sinusoidal, square, triangular and sawtooth. The user and/or therapist may adjust the amplitude, frequency and other factors of stimulation, for example, voltage, current and charge density and also may assign stimulation to specific electrode. The non-invasive electric stimulation frequency may include a spectral range from about 10 to about 300 Hz, for example, about 10-20 Hz, about 20-100 Hz or about 100-300 Hz. According to some embodiments, the electric stimulation pulse is preferably in the range of about 10 to 1000 μs in duration, negative/positive, monophasic or biphasic. The electric stimulation is configured to provide pulses of about 10% to 50% duty cycle.

Further, the stimulator may provide the stimulation in trains in the range up to the maximum defined frequency, which could be as low as 10-20 Hz or as high as 300 Hz. The stimulation can be provided as a constant-frequency train, as regular bursts of constant frequency stimuli, as random bursts, as bursts of gradually increasing/decreasing frequency, or in many other patterns that are determined in part by the reported sensations elicited in the patient. The stimulation is measured to be safe in terms of electrical current applied and effective in terms of stutter stop mode and cognitive training.

According to some embodiments, the electric stimulator is configured to transmit certain patterns of electric stimulation, which are essentially tailored to the user (i.e. person-specific). In an important embodiment of the invention, the electric stimulator transmits person-specific stimulation pattern, which is particularly effective at providing the stutterer with the trigger to stop the current stuttering mode. The device may be programmed to optimize such stimulation patterns while the choice of stimulation patterns can be controlled by the user or by the therapist. Stimulation parameters threshold can be determined by the lowest intensity of stimulation that is detected by the user and therapist as causing a sensation of stuttering modality without causing a noxious or painful sensation and keeping the stimulation safely below the threshold level for pain.

According to further embodiments, the device for stuttering alleviation may optionally include history record storage unit 106. The history record storage unit is configured to record and store history such as stuttering frequency and its types, speech samples and other signals during the stuttering. The unit is configured to record and save signals over manually or automatically defined periods of time. The unit is further configured to allow the user, the therapist and/or the technician to analyze the recorded stutterer's speech.

According to further embodiments, the device for stuttering alleviation may optionally include user interface 108. The user interface is configured to enable the PWS, the therapist and/or the technician to configure the device parameters, such as but not limited to stimulation strategy and to obtain recorded signals and statistics. The user interface is further configured to allow editing of the recorded signals, for example deleting part of the records. The user interface further allows recording initiation and termination.

The user interface may include: an interface such as, but not limited to, Bluetooth or USB for reading the history and/or graphical user interface on the device itself. According to alternative embodiments, the DSA is configured to be wirelessly connected to an external system, in order to provide such interface. The device is further configured to be wirelessly connected to a computer center to allow statistical processing of the data collected from all the patients treated by said device.

According to some embodiments, the device may further include button panel or touch screen 110 which allows the device parameters tuning, such as but not limited to the intensity of stimulation.

Figure 3:
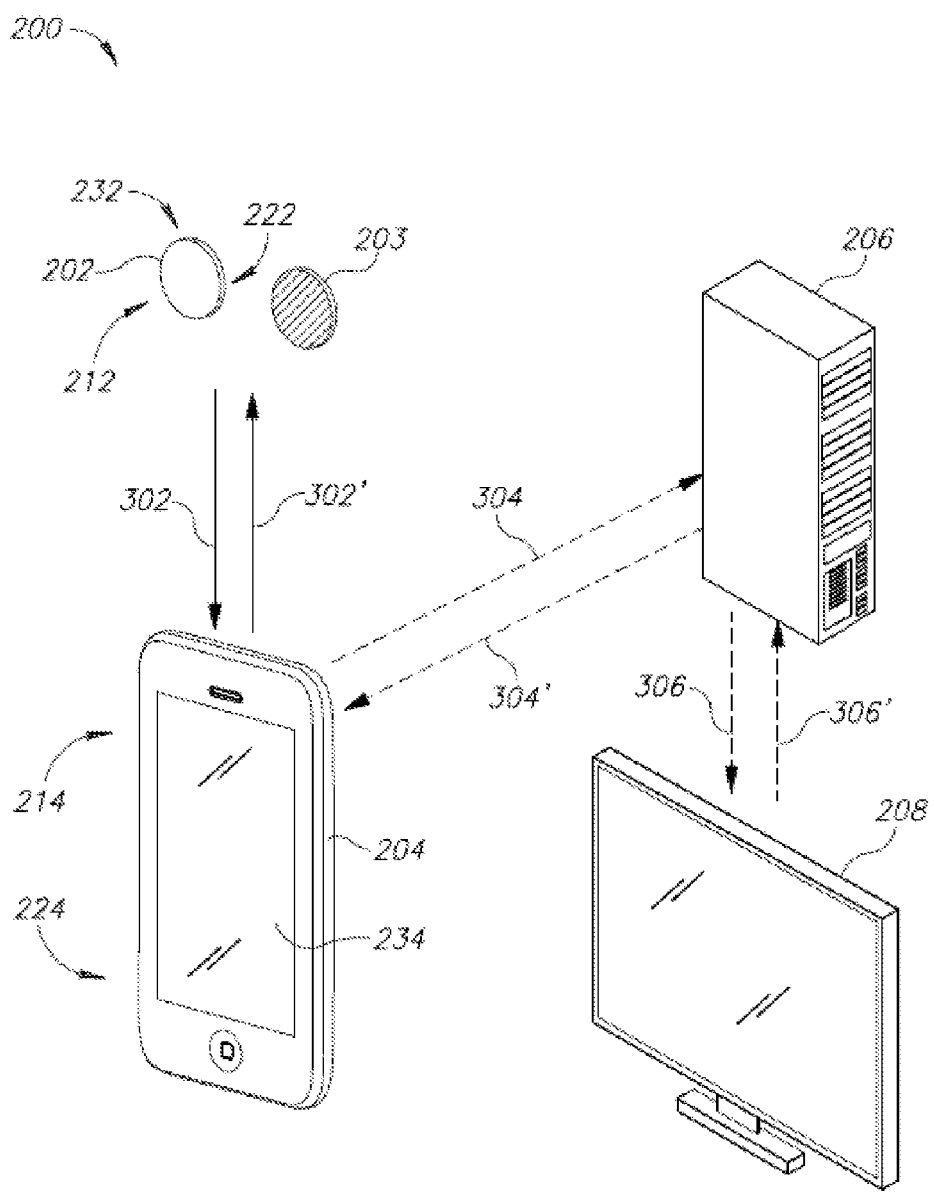
FIG. 3 schematically illustrates the components of the device for stuttering alleviation, further including a remote server and a server user interface.

Reference is made to FIG. 3 which schematically illustrates the components and mode of operation of the device for stuttering alleviation (DSA), in accordance with an embodiment of the invention. The claimed device for stuttering alleviation (DSA) is configured to maintain the studied speech fluency and accelerate the learning procedure for obtaining a permanent fluent speech. The DSA is further configured to employ a mobile device as a processing unit, providing a convenient use of the device. The device is further configured to enable the real-time analysis of stuttering and configuration of stimulation strategy by the speech therapist. The device is further configured to allow the use of data acquired by the device for research purposes.

Device for stuttering alleviation 200 includes speech sensor 202 and processing unit 204. According to further embodiments, device 200 includes stimulator 203, remote server 206 and server user interface 208.

According to some embodiments, speech sensor 202 is configured to output speech related signals. The speech sensor includes vocal cord compartment 212, acoustic compartment 222, or a combination thereof. The vocal cord compartment may include vocal cord activity detectors, such as but not limited to electromyograph (EMG), electroglottograph (EGG) or a combination thereof, as described hereinabove. According to some embodiments, acoustic compartment 222 may include sound detectors such as but not limited to microphone, noise-cancelling microphone or throat microphone. The acoustic compartment may further include a mobile handset microphone. Other devices adapted to detect pre-stuttering symptoms may be employed as sound detectors.

According to further embodiments, speech sensor 202 includes breathing compartment 232. The breathing compartment comprises a lung activity detector, configured to detect pre-stuttering symptoms related to breathing.

According to some embodiments, device for stuttering alleviation 200 includes stimulator 203. The stimulator is configured to receive stimulation indication from the processing unit. The stimulator may be a standalone unit (203) or may be a mobile device (not shown). The stimulator may preferably be a mechanic and/or electric stimulator, as described hereinabove. The stimulator is configured to generate tactile stimuli for directly affecting the stutterer. The stimulator may further be configured to provide visual stimulation. Stimulation parameters of the mechanical and the electric stimulators, such as mode, amplitude, frequency, duration and form are controlled by the processing unit and by remote server, in accordance with some embodiments. The stimulation is applied at predetermined intensities based on the stimulation rules provided by the processing unit. The stimulator may be provided with a control panel, comprising knobs, key buttons or other control elements, configured to allow activation, termination and/or intensity modulation of the stimulation by the user.

The speech sensor may be worn on a user's neck or chest. The stimulator may be worn on a wrist or a neck, on a belt as pager, or carried in a pocket. According to further embodiments, speech sensor and stimulator may form one unit (not shown). According to some embodiments, the speech sensor and stimulator unit may be worn on a user's body, for example on a user's neck. According to specific embodiments, the speech sensor and stimulator unit preferably has dimensions not larger than 60×30×9 mm and preferably its weigh does not exceed 50 g. According to further embodiments, the speech sensor and stimulator unit is connected to the processing unit by means of a connectivity component. The connectivity component may comprise a cable, and more preferably a wireless connection, such as Bluetooth. According to some embodiments, speech sensor and stimulator unit further includes a battery. According to further embodiments, the battery is sufficient for twenty four (24) hours of work without recharge.

Processing unit 204 includes stuttering detection program 214. The processing unit may further include stimulation generation program 224. According to some embodiments, the processing unit may be a standalone unit, as described hereinabove. According to preferred embodiments, processing unit 204 is a DSA application (APP) configured to run on a computer, including operation systems such as Windows (Microsoft) or a mobile device, including operating system such as iOS (Apple), Android (Google), Windows (Microsoft), QNX (RIM) Symbian (Accenture) or Linux. According to some embodiments, the mobile device is a mobile phone such as smartphone. Smartphones include, for example, iPhones™ (available from Apple Inc., Cupertino, Calif.), BlackBerries™ (available from RIM, Waterloo, Ontario, Canada), or any mobile phones equipped with the Android™ platform (available, for example, from Google Inc., Mountain View, Calif. or Samsung Group, South Korea). According to other embodiments, the mobile device is a tablet computer, available from, for example, Apple, Samsung, HTC, Motorola, RIM, Sony, Amazon, HP, Microsoft, Google, Asus, Toshiba, and Archos. According to additional embodiments, the mobile device is a personal digital assistant (PDA).

According to some embodiments, the application is configured to run as a standard application and does not require any additional elements in the hosting device. The application utilizes only standard documented operation system features. According to further embodiments, the application is configured to use the forward compatibility features of the hosting operational system, allowing the application to be installable and executable upon evolving of the hosting operation system versions. One of the important features of the present invention is that the processing unit operation does not require permanent internet connection. According to some embodiments, the computer or the mobile device may be connected to the internet at least once a day. The hosting computer or mobile device may be connected to internet by means of cellular connection, Wi-Fi, cable or other available connection modes.

According to some embodiments, the application is configured to increase battery consumption of the hosting mobile device by no more than 30%.

Stuttering detection program 214 is a program for the real-time detection of stuttering and identification of its mode and/or severity. The real-time detection and identification are based on speech signals received from speech sensor 202.

Several stuttering detection techniques known in art may be employed by the stuttering detection program. The most common way to assess disfluency is to transcribe the recorded speech and to locate occurrences of repetitions, syllable/word injections, prolongation, etc. speech (Howell et al., 1998). The speech segment durations measured are intervocalic intervals, stop-gaps, voice onset time, and vowel durations. The automatic recognition of stuttering and its classification may be performed by means of classification techniques, such as Artificial Neural Networks (ANNs), Hidden Markov Model (HMMs) and Support Vector Machine (SVM). Artificial Neural Networks (ANNs) are widely used in many ways in stuttering recognition, such as recognition of prolongation and repetition in stuttered speech, classification of fluent and disfluent in stuttered speech. This approach is described, for example, in [Peter et al.]. The ANNs model is used to detect the stuttered events. The particular stuttered events to be located are repetitions and prolongations. Studies on the vocal pitch (also called formant) and on higher formants (Howell & Williams, 1992; Czyzewski and Skorka, 1996; Kaczmarek and Skorka, 1997; Robb and Blomgren, 1997) may provide information on the articulation mechanisms present in stuttering. This approach is described, for example, in [A. Czyzewski et al., J. Intelligent Information Systems 21 (2) 2003 pp. 143-171].

The analysis performs segmentation of the speech signal and parameterization of the segments obtained. The parameters are constituted by the frequency of the vocal tone and the frequencies and amplitudes of the formants Feature vectors containing sequences of parameter values are subjected to correlation analysis and used as training material for some intelligent algorithms as rough sets and neural networks. As a result of the correlation analysis, information about the behavior of formants based on the spectrum of the signal of stuttered speech signal can be obtained. The application of intelligent algorithms allows for the automatic detection of stuttering artifacts.

Hidden Markov Model (HMM) is another approach towards stuttering recognition. HMM employs Markov process to model the changing statistical characteristics that are only probabilistically manifested through actual observation [T. Tian-Swee et al., "Application of Malay speech technology in Malay Speech Therapy Assistance Tools", Intelligent and Advanced Systems, 2007, International Conference on, 25-28 Nov. 2007, pp. 330-334]. Speech signal is assumed as a stochastic function of the state sequence of the Markov Chain. The state sequence itself is hidden.

SVM is used as classification tool in stuttering recognition, employing automatic detection method for syllable repetition in reading speech for objective assessment for stuttered disfluencies which has four stages consisting of segmentation, feature extraction, score matching and decision logic. The decision logic may be implemented using SVM to classify between fluent and disfluent speech [K. M. Ravikumar, R. Rajagopal, and H. C. Nagaraj, "An Approach for Objective Assessment of Stuttered Speech Using MFCC Features," ICGST International Journal on Digital Signal Processing, DSP, vol. 9, pp. 19-24, 2009].

According to some embodiments, the stuttering detection program is configured to identify a word and/or a phoneme related to stuttering. According to some embodiments, the stuttering detection program is further configured to identify stuttering modes, such as, but not limited to, prolongation, repetition, blocking and stress. According to further embodiments, the stuttering detection program is further configured to identify stuttering severity. The stuttering detection program may further be configured to identify stuttering level. The stuttering detection program is further configured to detect the stuttering mode in real time. According to some embodiments, the stuttering detection program is configured to detect stuttering no more than 500 ms following the stuttering event. According to the preferred embodiments, the stuttering detection program is configured to detect stuttering no more than 100 ms following the stuttering event. The program may further be configured to identify and associate the phoneme and/or the word in which the stuttering occurrence was detected. According to further embodiments, the stuttering detection program is configured to evaluate stuttering severity according to the 0-100% scale. The stuttering detection program may be configured to evaluate stuttering level according to the 0-100% scale. The stuttering detection program may be configured to evaluate stuttering level according to the 1-10 scale, 1-5 scale or any other scale, for example, 1 being the most severe case and 10 or 5 being the least severe case of stuttering, or vice versa. According to still further embodiments, the stuttering detection program is configured to evaluate stuttering confidence according to the 0-100% scale. According to yet further embodiments, the stuttering detection program is configured to allow the speech therapist to configure the basic parameters for stuttering detection. The stuttering detection parameters may be selected from but not limited to threshold length of prolongation, threshold number of repetitions threshold length of blocking and threshold level of stress. According to other embodiments, the threshold can be automatically detected, learned and adapted by the device.

According to some embodiments, the detection accuracy of the stuttering detection program is above 95% in cases of fluency and above 70% in cases of disfluency. According to preferred embodiments, the detection accuracy of the stuttering detection program is above 99% in cases of fluency and above 80% in cases of disfluency.

According to an important embodiment, the stuttering detection program is configured to allow the stuttering detection without elimination of background noise. Furthermore, the accuracy of detection is not affected by the background or conversational noise.

According to some embodiments, the DSA processing unit is configured to log and record stuttering occurrences. The stuttering log may include parameters related to stuttering, detected by the stuttering detection program and/or calculated therefrom, such as but not limited to: a word spoken, a phoneme spoken, stuttering mode, stuttering severity and stuttering confidence level or any other parameter or any combination thereof. The stuttering occurrence log may further include date, time of day or any combination thereof. The personal stuttering occurrence record may be used for analysis by the speech therapist and the anonymous log for research purposes. The stuttering log may further be used to configure the stimulation rules. According to some embodiments, the processing unit is further configured to record the disfluent speech upon the detection of stuttering occurrence. The stuttering log may further include the recorded speech related to stuttering, comprising the speech before, during and after the stuttering occurrence. The processing unit is further configured to allow the user and speech therapist to modulate the recorded speech length before and after the stuttering occurrence. According to some embodiments, the application is further configured to allow the user to control the voice recording.

Stimulation generation program 224 is a program for real time decision on generating stimulation and its type based on the stuttering occurrence parameters/characteristics. The stuttering occurrence parameters/characteristics may include a word spoken, a phoneme spoken, stuttering mode, stuttering severity, time of day, location or any combination thereof.

According to some embodiments, stimulation generation program 224 is configured to transfer stimulation indication to stimulator 203. According to further embodiments, the stimulation generation program is configured to allow multiple types of the stimulator operation, such as electric stimulation, mechanic, stimulation or any combination thereof. The stimulation generation program is further configured to allow visual stimulation. According to some embodiments, the visual stimulation is a visual effect provided by the user interface of the processing unit. According to some embodiments, the mechanic stimulation is provided by the mobile device. According to further embodiments, the mechanic stimulation is a vibration provided by the mobile device or by an external stimulator 203, induced by the processing unit The stimulation generating program is further configured to allow modulation of the stimulation parameters, such as, but not limited to stimulation intensity, mode, amplitude, frequency, duration, form and/or pattern. The stimulation generation program is configured to provide default rules for negative feedback stimulation. The stimulation generation program is further configured to allow the speech therapist to define stimulation rules. Said rules may be defined in the form: If {combination of syllable AND stuttering mode AND severity AND confidence} then {stimulation parameter}. According to further embodiments, stimulation rules may be defined in the form: If {time-of-day} then {stimulation on} else {stimulation off}. According to still further embodiments, stimulation rules may be defined in the form: If {accuracy of (combination of syllable AND stuttering mode AND severity AND confidence)}>{X} then {stimulation on} else {stimulation off}. The default rules and the rules defined by the speech therapist may be used by the stimulation generation program in the online or the offline operation mode of the processing unit. The stimulation rules may further be configured such that stimulation is applied only at a specific rate relative to stuttering occurrences, for example in 20% of stuttering events. According to some embodiments, the processing unit is configured to allow the user to control the stimulation intensity.

The processing unit may further include user interface (UI) 234. The user interface is configured to enable the user to activate and terminate stuttering detection and voice recording. The user interface is further configured to allow the user to delete the recorded speech related to stuttering. The UI further provides indication of stuttering upon its detection, comprising presenting the stuttering log, speech related to stuttering recording or combination thereof. The UI is configured to allow the user to choose the data to be presented. The user interface further provides metric for stuttering evaluation and presents stuttering trends. The user interface may further provide tools for stuttering evaluation. The UI allows the user to configure parameters related to stuttering detection, such as length of prolongation, threshold number of repetitions threshold length of blocking and threshold level of stress. The UI is further adapted to allow the user to configure the data to be included in the stuttering log, such as word spoken, phoneme spoken, stuttering mode, stuttering severity, time of day, location and/or stuttering probability. The UI further allows the user to modulate the length of speech to be recorded before and after the stuttering occurrence.

The user interface is further configured to enable the user to activate or terminate the stimulation. The UI further enables the user to modulate stimulation parameters, such as stimulation intensity, type, mode, amplitude, frequency, duration, form and/or pattern. According to further embodiments, the user interface allows the user to configure stimulation rules, wherein the stimulation rules are based on the stuttering occurrence parameters and/or characteristics. The user interface may further be configured to allow the user to determine stimulation rules based on the stuttering log. According to some embodiments, the user interface is configured to provide visual stimulation.

According to some embodiments, the device for stuttering alleviation further includes remote server 206. The remote server may be a servers farm or may be located on a server computing cloud. The remote server is configured to allow the remote access to the processing unit of the device. Said remote server is further configured to serve as central repository of patients, logs and recordings. The remote server is further adapted to enable online monitoring of patients by a speech therapist. According to some embodiments, the remote server provides said online monitoring seven (7) days a week, twenty four (24) hours a day.

According to some embodiments, the remote server is configured to support a predetermined amount of speech therapists, such as about ten thousand (10000) therapists and a predetermined amount of patients, such as about one million (1000000) patients. The remote server is further configured to support an average speech time of about one (1) hour a day, at a stuttering ratio of about 25%. According to further embodiments, the server is configured to support and store data from the treatment, the duration of which is about two (2) years.

The remote server is configured to act as a license server. The remote server is configured to provide licenses to the processing unit and to the server user interface application, thereby providing licenses to the users and to the speech therapists.

The remote server is configured to receive and store the data recorded by the processing unit. According to some embodiments, the remote server is configured to receive and store the stuttering occurrence record and speech recorded during stuttering. Such data may be used by the speech therapist for stimulation rules determination, patient's stuttering analysis and stuttering trends evaluation. In may further be used as a database for academic and/or medical research.

According to further embodiments, the remote server is configured to transmit the parameters defined by means of the server user interface, such as the recording length before and after stuttering occurrence and stuttering detection parameters. The remote server is further configured to transmit default stimulation rules and stimulation rules configured by the speech therapist to the processing unit.

According to some embodiments, the device for stuttering alleviation further includes server user interface (SUI) 208. The server user interface may be a remote user interface. The server user interface is a web application configured to be viewed by the speech therapist. The SUI is graphically designed for optimal user experience of the speech therapist. The server user interface is configured to process the data received from the remote server. According to some embodiments, the SUI is configured to run on the remote server. The server user interface is configured to use standard mechanisms, protocols and building blocks. According to further embodiments, the SUI uses secured protocols, such as HTTPS, between the browser and the remote server. The server user interface is configured to allow the therapist to access only his patients.

The SUI is configured to enable the therapist to monitor the patient's speech, define the stimulation rules strategy and configure logging and recording. Patient's speech monitoring can be conducted during clinical sessions and in real time. According to some embodiments, stimulation strategy may be defined when the processing unit is operating in an online mode. According to other embodiments, the stimulation strategy may be defined when the processing unit is operating in an offline mode, based on the existing logs and records. The server user interface is further configured to allow the speech therapist to register licensed users and to conduct research.

According to further embodiments, the server user interface is configured to allow the speech therapist to configure the recording length before and after stuttering occurrence. The SUI is configured to allow the speech therapist to configure stuttering detection parameters, the recording length before and after stuttering occurrence, to provide default stimulation rules and to allow the speech therapist to define the rules, based on the stuttering occurrences and time-of-day, as described hereinabove.

According to further embodiments, the SUI is configured to allow the therapist to manage patients. The server user interface includes independent records of each patient, including details such as, but not limited to patient's name, ID, date of birth, gender and notes. The SUI is configured to allow the therapist to add or to remove patients and/or patients' details from the remote server. The SUI is further configured to maintain confidentiality of patients' data.

The server user interface further provides the means for analysis of the detected and recorded disfluency. The analysis means may include metrics such as but not limited to frequency of stuttering, frequency of stuttering modes and average severity of stuttering occurrence. The analysis means may further include graphical representation of the metric trends. According to further embodiments, the SUI is configured to provide a table of all stuttering occurrences and a play button for replaying the acoustic recordings. The SUI further provides the means for filtering and sorting of the table.

According to some embodiments the SUI is configured to log all the configuration activity by the therapist and by the user. The SUI is further configured to enable a therapist to export the stuttering data and recordings to perform an offline research. According to some embodiments, the STD is configured to allow the therapist to define the events requiring a real-time alerting by the processing unit.

According to some embodiments, the device for stuttering alleviation includes unidirectional and bidirectional interfaces, configured to send and/or receive specific type of information, as denoted by arrows 302, 302', 304, 304', 306 and 306'.

Interface 302 is the interface providing processing unit 204 with speech sensory signals from the sensor. The speech sensory signals are selected from acoustic speech signal, electromyograph signal, electroglottograph signal, breathing compartment signal and any combination thereof. The interface operates as a standard speech feed from a mobile earpiece, wire line and/or wireless.

Interface 302' is the interface providing the stimulator with stimulation indication from processing unit 204. The stimulation commands are generated by stimulation generation program 224 and may comprise parameters such as, but not limited to, mode, intensity, frequency and amplitude. The interface is adapted to operate as an earphone signal from a mobile earpiece, wire line and/or wireless, using a coding such as, for example, dual-tone multi-frequency signaling (DTMF).

Interface 304 is the interface providing the remote server with information from the processing unit 204. The information transferred from the processing unit comprises the logs and recordings acquired by the processing unit, such as stuttering occurrence record, the speech recording during stuttering and user's stimulation alleviation. The information transferred from the processing unit further comprises real-time alerts, such as but not limited to the cases of extreme stuttering. The interface operates through a standard TCP/IP or UDP/IP protocol. The logs and recordings are transferred to the management program periodically, such as during clinical meetings or whenever the Wi-Fi is available.

Interface 304' is the interface providing the processing unit with data from the remote server. The data transferred from the remote server comprises the parameters determined by the speech therapist by means of the server user interface, such as speech related to stuttering, stuttering detection parameters and stimulation rules. The interface is configured to send configuration updates, software upgrades and license keys to the DSA application. The interface is further configured to transfer real-time alert requiring events configured by the speech therapist. The interface operates through a standard TCP/IP or UDP/IP protocol.

Interface 306 is the interface providing the server user interface with information from the remote server. The server user interface is configured to process the logs and recordings transferred from the processing unit to the remote server. The interface operates through a standard HTTP interface.

Interface 306' is the interface providing the remote server with information from the server user interface application. The information generated by the SUI comprises the recording and treatment parameters configured by the speech therapist, such as speech related to stuttering, stuttering detection parameters, stimulation rules and real-time alert requiring events. The interface operates through a standard HTTP interface.

In the description and claims of embodiments of the present invention, each of the words, "comprise" "include" and "have", and forms thereof, are not necessarily limited to members in a list with which the words may be associated.

The invention has been described using various detailed descriptions of embodiments thereof that are provided by way of example and are not intended to limit the scope of the invention. The described embodiments may comprise different features, not all of which are required in all embodiments of the invention. Some embodiments of the invention utilize only some of the features or possible combinations of the features. Variations of embodiments of the invention that are described and embodiments of the invention comprising different combinations of features noted in the described embodiments will occur to persons with skill in the art.

What is claimed is:

1. A speech training device comprising:
    a speech sensor comprising a microphone, said speech sensor configured to output a signal indicative of speech; and
    a processing unit configured to:
        receive the signal indicative of speech;
        detect stuttering in the signal indicative of speech by searching for prolongations, repetitions, blocking and stress in the speech;
        determine a level of stuttering based on an analysis of the detected stuttering in the signal indicative of speech; and
        produce a stimulation indication by applying stimulation rules on the determined level of stuttering, wherein the stimulation comprises a visual stimulation indicative of the determined level of stuttering.

2. The device according to claim 1, wherein the speech sensor further comprises a vocal cord compartment, a breathing compartment or a combination thereof.

3. The device according to claim 2, wherein the vocal cord compartment comprises a vocal cord activity sensor.

4. The device according to claim 3, wherein the vocal cord activity sensor comprises electromyograph (EMG), electroglottograph (EGG) or a combination thereof.

5. The device according to claim 2 wherein the breathing compartment comprises a lung activity sensor.

6. The device according to claim 1, wherein the processing unit is a standalone unit.

7. The device according to claim 1, wherein the processing unit is an application configured to run on a computer or a mobile device.

8. The device according to claim 7, wherein the mobile device comprises operating system, comprising iOS (Apple), Android (Google), Windows (Microsoft), QNX (RIM), Symbian (Accenture), or Linux.

9. The device according to claim 1, wherein the processing unit is configured to detect stuttering in a real time.

10. The device according to claim 1, wherein the processing unit is configured to allow determination of stuttering detection parameters.

11. The device according to claim 10, wherein the stuttering detection parameters comprise threshold length of prolongation, threshold number of repetitions, threshold length of blocking, threshold level of stress or any combination thereof.

12. The device according to claim 1, wherein the processor is further configured to log the detected stuttering; wherein stuttering logging comprises saving and/or outputting the detected stuttering.

13. The device according to claim 12, wherein the stuttering log comprises word spoken, phoneme spoken, stuttering mode, stuttering severity, stuttering confidence level, date, time of day, location or any combination thereof.

14. The device according to claim 12, wherein the stuttering log may be used for analysis by a speech therapist.

15. The device according to claim 1, further comprising a stimulator; wherein the stimulator is a standalone unit.

16. The device according to claim 1, further comprising a stimulator wherein the stimulator and the speech sensor form one unit.

* * * * *